United States Patent [19]

Scardera et al.

[11] 4,317,940
[45] Mar. 2, 1982

[54] BIODEGRADABLE SURFACTANTS

[75] Inventors: Michael Scardera, Hamden; Frank R. Grosser, Bethany, both of Conn.

[73] Assignee: Olin Corporation, New Haven, Conn.

[21] Appl. No.: 219,555

[22] Filed: Dec. 23, 1980

[51] Int. Cl.³ .............................................. C07C 43/11
[52] U.S. Cl. .............................. 568/625; 252/DIG. 6; 252/351; 252/DIG. 1
[58] Field of Search ........................ 568/625, 624, 608

[56] References Cited

U.S. PATENT DOCUMENTS

| | | |
|---|---|---|
| 2,174,761 | 10/1939 | Schuette et al. |
| 2,674,619 | 4/1954 | Lundsted |
| 2,677,700 | 5/1954 | Jackson et al. |
| 3,382,285 | 5/1968 | Egan et al. |
| 3,956,401 | 5/1976 | Scardera et al. ................ 568/625 |

*Primary Examiner*—Bernard Helfin
*Attorney, Agent, or Firm*—William A. Simons; Thomas P. O'Day

[57] ABSTRACT

Described are biodegradable surfactants useful as agricultural emulsifiers and having the formula:

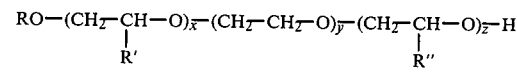

wherein R is a linear, alkyl hydrocarbon chain having an average from about 6 to about 10 carbon atoms; R' is a linear, alkyl hydrocarbon of 1 to about 4 carbon atoms; R'' is a linear, alkyl hydrocarbon of from 1 to about 4 carbon atoms; x is an integer from about 8 to about 12; y is an integer from about 19 to about 25; and z is an integer from about 2 to 7.

6 Claims, No Drawings

BIODEGRADABLE SURFACTANTS

BACKGROUND OF THE INVENTION

1. Field of the Invention

This invention relates to biodegradable surfactants which may be used as agricultural emulsifiers.

2. Description of the Prior Art

The surface active agent art is quite old and replete with different compositions of useful ionic and nonionic surfactants. An early patent to Schuette et al, U.S. Pat. No. 2,174,761, broadly discloses the preparation of high molecular weight surfactants by the sequential additional of propylene oxide and ethylene oxide to long chain hydrophobic alcohols and specifically discloses the production of surfactants which are solids at room temperature. More recent patents to Lunsted, U.S. Pat. No. 2,674,619 and Jackson et al. U.S. Pat. No. 2,677,700 show surfactant compositions prepared by the addition of propylene oxide and ethylene oxide to a reactive hydrogen compound. Schick discloses the more recent history of nonionic surfactants in his book "Nonionic Surfactants", 1967. Canadian Pat. No. 540,359 describes conjugated polyoxypropylenepolyoxyethylene compounds as surfactants which are prepared by condensing propylene oxide with an alcohol to obtain a polyoxypropylene intermediate polymer and subsequently condensing ethylene oxide with the intermediate polymer to obtain the final product. The Canadian patent requires the use of an alcohol which has a detergency factor of less than 100, i.e., alcohols, if linear, having six or less carbon atoms.

Recent environmental problems have placed particular emphasis on surfactants that are biodegradable. Biodegradability is defined as that property possessed by a material which is capable of being decomposed by bacteria or living organisms, as described for example in the patent to Egan et al, U.S. Pat. No. 3,382,285, while the prior art, as noted above, has disclosed a large number of surfactant products having a wide variety of properties, there has been some difficulty in obtaining surfactants which are effective emulsifiers for agricultural pesticidal solutions, especially those made up a xylene and water, and are also biodegradable.

A recent patent to Scardera and Scott, U.S. Pat. No. 3,956,401 described a low foaming, biodegradable, liquid, non-gelling and nonionic surfactants which has found particular usefulness in automatic dishwashing detergent formulations. However, the surfactants described in that patent have little or no applicability as emulsifiers. An emulsion is usually a dispersion of two mutual insoluble liquids (e.g., water and oil). Emulsifiers or emulsifying agents are used to stabilize the dispersion of these two insoluble liquids. A more complete discussion of emulsions and emulsifying agents can be found in *Practical Emulsions*, written by H. Bennett, J. C. Bishop, Jr., and M. F. Wulfinghoff and published by Chemical Publishing, Inc., N.Y. (1968), pages 6 to 8.

Now it has been found that the compounds of this invention are nonionic, biodegradable surfactants which are particularly suitable as agricultural emulsifiers, especially in xylene/water solutions.

BRIEF SUMMARY OF THE INVENTION

Accordingly, the present invention is directed tobiodegradable surfactants useful as agricultural emulsifiers and having the formula:

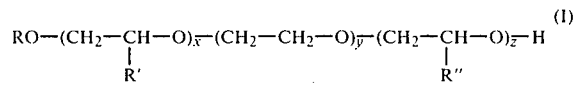

wherein R is a linear, alkyl hydrocarbon chain having an average from about 6 to about 10 carbon atoms; R' is a linear, alkyl hydrocarbon of 1 to about 4 carbon atoms; R" is a linear, alkyl hydrocarbon of from 1 to about 4 carbon atoms; x is an integer from about 8 to about 12; y is an integer from about 19 to about 25; and z is an integer from about 2 to 7.

DETAILED DESCRIPTION

The surfactant compounds of Formula (I) may be prepared by the well-known methods of adding an alkylene oxide compound to an alcohol as shown for example in Schick's "Nonionic Surfactants" at page 102 and in U.S. Pat. No. 2,677,700 at Column 6. Generally, the compounds (I) may be prepared by reacting a primary, linear, monohydric alcohol having from about 6 to 10 carbon atoms with an alkylene oxide such as propylene oxide in the desired amounts at an elevated temperature in the presence of alkaline catalysts such as the salts or hydroxides of the alkali metals or the alkaline earth metals. Following this ethylene oxide is added in the desired amounts using the same conditions to obtain an intermediate alcohol-polyoxyalkylene-polyoxyethylene reaction product. Next, an alkylene oxide, such as propylene oxide, is reacted with the intermediate product in the desired amounts, by again using the same type of catalyst and reaction conditions, to obtain the low foaming surfactant products of the present invention.

As noted above, the alcohol used is a primary linear alcohol having 6 to 10 carbon atoms. A mixture of such alcohols may be used and this is generally true when using commercial alcohols which are often available as a blend of several alcohols. Consequently, the number of carbon atoms in the alcohol is referred to as an average number and such number can be determined by vapor phase chromatography (VPC) and the hydroxyl number. Also, as noted above, while the alcohols are referred to as linear, there may be some minor amount of branching particularly due to the method of manufacture. Following are some of the useful alcohols, hexyl alcohol, and well-known commercial mixtures such as ALFOL 610 having an average of about 8.2 carbon atoms (about 20% of $C_6$, 35% of $C_8$, and 44% of $C_{10}$) produced by Continental Oil Co. and EPAL 610 (about 17% of $C_6$, 37% of $C_8$, and 46% of $C_{10}$) produced by Ethyl Corporation of Baton Rouge, LA. Further illustrations of such alcohols and of their method of preparation are shown in Schick's "Nonionic Surfactants" at pages 87–90.

The alcohols used as one of the reactants in preparing the surfactants of the present invention, in addition to being generally primary, linear, monohydric alcohols having an average number of carbon atoms of about 6 to 10 and preferably about 8 to 9, have a detergency factor of greater than 100. By using a linear alcohol or a mixture of linear alcohols having a detergency factor of greater than 100, yet having an average number of carbon atoms no greater than 10, nonionic surfactants are obtained which are biodegradable.

The R group, as noted above, is substantially or predominantly linear which means there is essentially no branching. This is important because the biodegradability of the product is detrimentally affected by branching. However, as will be described in more detail below, the R group is derived from a linear alcohol and generally from a mixture of alcohols. Due to the nature of the process by which these alcohols are prepared, there may be small amounts of branched chain alcohols present. Generally, the presence of such branched chain alcohols in amounts less than about 15% of the total alcohol content by weight, will not adversely effect the overall properties of the final product. The terms linear or substantially linear hydrocarbon when used in the specification and claims with respect to R are intended to include such small amounts of branching as defined above. The number of carbon atoms referred to for R is an average number since commercial grade alcohols are generally a mixture of more than one alcohol. Preferably, the R group will have an average of about 8 to 9 carbon atoms.

The alkylene oxide reactants of the present surfactant (I) such as ethylene oxide (EO) and propylene oxide (PO) are well known commodity chemicals and are widely available. Both R' and R" are preferably 1 to 2 carbon atoms and most desirably, 1 carbon atom. Thus, propylene oxide is the preferred alkylene oxide for these two adduct chains; although higher alkylene oxides like butylene oxide or hexylene oxide may also be used.

The values of the x, y, and z integers are actually average numbers determined by the weight of that particular reactant which is used.

In preparing the surfactants of the present invention, a temperature of about 140° to about 200° C. may be used in the reaction and the catalyst (preferably an alkali hydroxide such as potassium hydroxide) concentration can be varied widely with about 0.001 to about 1% by weight of catalyst based on the weight of alcohol being generally used. While the reaction may be carried out at atmospheric pressure, it may also be performed under elevated pressure conditions if desired. Preferably, the amount of catalyst is from about 0.3% to about 0.5% by weight of the alcohol used. However, it is to be understood that the present invention is not to be limited to any particular method of preparation.

The surfactant products (I) of this invention may be used in a variety of applications such as detergent formulations, as wetting, washing, and dispersing agents in the textile, leather, paper, paint, pharmaceutical and cosmetic industries, as well as for household applications. Their preferred use is in pesticidal solutions (e.g., xylene/water solutions) used in the crop protection area.

The following examples further illustrate the present invention. All parts and percentages are by weight unless otherwise explicitly indicated.

EXAMPLE 1

In a 3-necked, 500 ml round-bottom flask fitted with a dropping funnel, nitrogen inlet, stirrer, dry ice condenser and vent, Alfol 610 alcohol[1] [33.5 grams (0.25 moles) (a mixture of $C_6$, $C_8$ and $C_{10}$ linear alcohols)] and potassium hydroxide [10.3 grams (0.005 moles)] were added. Under a nitrogen atmosphere, propylene oxide [170.3 grams (2.93 moles)] was then added dropwise to the alcohol at 160° C. to 180° C. The reaction cooled, weighed (204.1 grams) and the alcohol:propylene oxide ratio calculated (1:11.7).

[1] Manufactured by Conoco Petrochemicals, Continental Oil Co., located at New York, N.Y.

One-half of the alcohol-PO adduct (102 grams) was recharged into the flask, heated to 160° C.–166° C. and ethylene oxide [134.4 grams (2.98 moles)] was added dropwise. This intermediate product was then reacted with propylene oxide [19.9 grams (0.34 moles)] under the same conditions noted above. The product was subsequently cooled and neutralized with acetic acid. The product weight was 253.3 grams and the cloud point was 68° C. in a 1% by weight water solution of the product. The molecular weight of the final product was 2012 with an alcohol:PO:EO:PO molar ratio as shown in Table I, below.

Example 1 may be repeated substituting a higher alkylene oxide for the propylene oxide in preparing the adduct of the first step and/or substituting a higher alylne oxide for the propylene oxide in the last step of preparing the surfactants of the present invention. For example, 2.93 moles of butylene oxide or hexylene oxide may be substituted for the 2.93 moles of propylene oxide used in the first step of Example 1 above. Also, about 0.34 moles of butylene oxide or hexylene oxide may be substituted for the propylene oxide used in the last step of Example 1 above.

EXAMPLES 2-4

Example 1 was repeated except using other molar ratios of alcohol:PO:EO:PO. The amounts reacted and calculated ratios of products (along with the molecular weight) are given in Table I.

All four adducts were semi-solid (slush to solid and their surface properties are also shown in Table I.

TABLE I

|  | Example 1 | Example 2 | Example 3 | Example 4 |
| --- | --- | --- | --- | --- |
| Amounts Added to Reactor |  |  |  |  |
| Alcohol-Moles | 0.25 | 0.5 | 0.25 | 0.25 |
| PO-Moles | 2.93 | 3.98 | 2.54 | 2.93 |
| EO-Moles | 2.98 | 9.73 | 2.81 | 3.03 |
| PO-Moles Terminal | 0.34 | 1.22 | 0.35 | 0.77 |
| Calculated Reacted Mole Ratios |  |  |  |  |
| Alcohol-Moles | 1 | 1 | 1 | 1 |
| PO-Moles | 11.7 | 8.0 | 10.2 | 11.7 |
| EO-Moles | 23.9 | 19.5 | 22.5 | 24.2 |
| PO-Moles-Terminal | 2.7 | 2.4 | 2.8 | 6.1 |
| Cloud Point, °C. | 68 | 75 | 73 | 66 |
| Surface Tension dynes/cm - 0.1 wt. % | 34.0 | 30.4 | 30.4 | 29.1 |
| Interfacial Tension vs. mineral oil [dynes/cm 0.1 wt. %] | 2.8 | 4.8 | 3.3 | 2.6 |
| Draves Wetting Time[2], at 25° C. |  |  |  |  |
| 0.10 wt. % in $H_2O$ | 66 sec. | 73 sec. | 83 sec. | 44 sec. |

TABLE I-continued

| | Example 1 | Example 2 | Example 3 | Example 4 |
|---|---|---|---|---|
| 0.25 wt. % in H$_2$O | 17 sec. | 17 sec. | 15 sec. | 14 sec. |
| 0.50 wt. % in H$_2$O | 7 sec. | 5 sec. | 7 sec. | 6 sec. |
| at 60° C. | | | | |
| 0.10 wt. % in H$_2$O | 23 sec. | 18 sec. | 21 sec. | 23 sec. |
| 0.25 wt. % in H$_2$O | 8 sec. | 6 sec. | 7 sec. | 7 sec. |
| 0.50 wt. % in H$_2$O | 5 sec. | 3 sec. | 4 sec. | 4 sec. |
| Ross-Miles Foam Height mm initial/after 5 mins.[3] at 25° C. | | | | |
| 0.10 wt. % in H$_2$O | 80/15 mm | 115/20 mm | 80/15 mm | 75/15 mm |
| 0.25 wt. % in H$_2$O | 115/15 mm | 140/20 mm | 115/15 mm | 105/20 mm |
| 0.50 wt. % in H$_2$O | 145/20 mm | 170/25 mm | 115/20 mm | 120/15 mm |
| at 60° C. | | | | |
| 0.10 wt. % in H$_2$O | 25/15 mm | 90/10 mm | 55/15 mm | 35/20 mm |
| 0.25 wt. % in H$_2$O | 60/15 mm | 135/15 mm | 100/15 mm | 45/15 mm |
| 0.50 wt. % in H$_2$O | 120/15 mm | 155/15 mm | 125/15 mm | 90/15 mm |

[2]ASTM Method D-2281-68
[3]ASTM Method D-1173-56

EXAMPLES 5–8 and COMPARISONS 1–2

The surfactants described in Examples 1–4 were evaluated for emulsification properties in water-xylene mixtures. The procedure consisted of dissolving two grams of surfactant in 25 ml distilled water. The solution was then added to 25 ml xylene in a 50 ml emulsion tube and shaken for 30 seconds. The emulsion tube was then placed in an Atlab Emulsion Viewer. The stability of the emulsion is measured by the length of time until "creaming" or breaking of the emulsion occurs. The longer the time, the greater the stability of the emulsion system. The results of this study, along with comparisons of two other types of nonionic surfactants are shown in Table II. The results indicate the excellent emulsion stability of the surfactants described in Examples 1–4.

TABLE II

| Example or Comparison | Surfactant (2g) | Emulsion Stability (water-xylene) |
|---|---|---|
| Example 5 | Product of Example 1 | greater than 8 hours |
| Example 6 | Product of Example 2 | greater than 8 hours |
| Example 7 | Product of Example 3 | greater than 8 hours |
| Example 8 | Product of Example 4 | greater than 8 hours |
| Comparison 1 | C$_{6-10}$ alcohol-3PO-12EO-18PO | breaks in 5 minutes |
| Comparison 2 | C$_{9-11}$ alcohol-8EO | breaks in 12 minutes |

EXAMPLE 9 AND COMPARISONS 3–7

The adduct prepared according to Example 2 and five other surfactants were tested as agricultural emulsifiers in water-xylene pesticidal mixtures. Specifically, six emulsion conentrates were first prepared. These emulsion concentrates each contained 25% by weight of pentachloronitrobenzene (a well-known fungicide), 72% by weight xylene, 1.5% by weight calcium dodecylbenzene sulfonate and 1.5% of one of the different surfactants listed below in Table II. Next, five grams of each of these six emulsuion concentrates was added to 100 ml of water having 342 ppmhardness. The emulsion stability of each of these six emulsions were evaluated by determining the length of time until breaking of the emulsion occurred. The results of this evaluation are given in Table II. As can be seen, the surfactant of the present invention has much greater emulsion stability than the other surfactants.

TABLE III

| Example or Comparison | Surfactant | Emulsion Stability |
|---|---|---|
| Example 9 | Adduct of Example 2 | greater than 8 hours |
| Comparison 3 | Calcium dodecylbenzene sulfonate | breaks in 15 minutes |
| Comparison 4 | C$_{12-15}$ alcohol-12EO | breaks in 2 hours |
| Comparison 5 | Nonylphenol-9EO | breaks in 2 hours |
| Comparison 6 | C$_{13}$ alcohol-14EO | breaks in 2 hours |
| Comparison 7 | H-11EO-16PO-11EO-OH | breaks in 1 hour |

What is claimed is:

1. A compound having the formula:

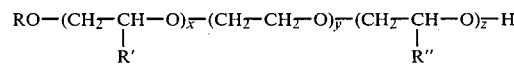

wherein R is a linear, alkyl hydrocarbon having an average of from about 6 to about 10 carbon atoms; R' is a linear, alkyl hydrocarbon of 1 to about 4 carbon atoms; R" is a linear, alkyl hydrocarbon of from 1 to about 4 carbon atoms; x is an integer from about 8 to about 12; y is an integer from about 19 to about 25; and z is an integer from about 2 to 7.

2. The compound of claim 1 wherein R has an averrage of about 8 to about 9 carbon atoms.

3. The compound of claim 1 wherein R' has 1 to 2 carbon atoms.

4. The compound of claim 1 wherein R" has about 1 to 2 carbon atoms.

5. The compound of claim 1 wherein both R' and R" have 1 to 2 carbon atoms.

6. The compound of claim 1 wherein both R' and R" are methyl groups.

* * * * *